United States Patent [19]

Jarcho et al.

[11] 4,195,366
[45] Apr. 1, 1980

[54] WHITLOCKITE CERAMIC

[75] Inventors: Michael Jarcho; Ronald L. Salsbury, both of Schodack, N.Y.

[73] Assignee: Sterling Drug Inc., New York, N.Y.

[21] Appl. No.: 863,721

[22] Filed: Dec. 23, 1977

[51] Int. Cl.$^2$ .......................... A61F 1/24; A61K 5/01; C09K 3/00; C04B 35/00
[52] U.S. Cl. ......................................... 3/1.9; 106/35; 106/40 R; 106/39.5; 128/92 C; 423/311; 433/201; 433/202
[58] Field of Search ....................... 106/39.5, 63, 40 R, 106/35; 3/1.9; 32/10 A; 128/92 C; 423/311

[56]  References Cited

U.S. PATENT DOCUMENTS

| 3,913,229 | 10/1975 | Driskell et al. | 35/15 |
| 3,929,971 | 12/1975 | Roy | 423/308 |
| 4,097,935 | 7/1978 | Jarcho | 106/39.5 |

FOREIGN PATENT DOCUMENTS 381030  6/1972 Spain.

OTHER PUBLICATIONS

Bett et al., "Hydroxyapatite Catalysts" J. A. Chem. Soc. 89, 5535 (1967).

Kutty, T. R., "Thermal Decomposition of Hydroxylapatite," Indian J. Chem. II, 695 (1973).

Leclerq, P., "Evolution Thermique du Systeme Sulfate d'Ammonium-Phosphate de Calcium," Thermal Analysis 2 (1971), pp. 229-238.

Driskell, T. D. et al., "Significance of Resorbable Bioceramics in the Repair of Bone Defects," Proceedings of 26th Annual Conference Engineering in Medicine and Biology 15, 199 (1973).

Levin, M. P. et al., "A Comparison of Iliac Marrow Biodegradable Ceramic in Periodontal Defects," J. Biomed. Mater. Res., vol. 9, pp. 183-195 (1975).

Getter, L. et al., "Three Biodegradable Calcium Phosphate Slurry Implants in Bone," J. Oral Surgery, vol. 30 (1972), pp. 263-268.

Bhaskar, S. et al., "Biodegradable Ceramic Implants in Bone," Oral Surgery, vol. 32, pp. 336-346 (1971).

Primary Examiner—John H. Mack
Assistant Examiner—Mark Bell
Attorney, Agent, or Firm—Paul E. Dupont; B. Woodrow Wyatt

[57]  ABSTRACT

A novel, polycrystalline whitlockite ceramic in either pore-free or porous form, processes for the preparation thereof and methods of using the same as biological implant materials are disclosed.

21 Claims, No Drawings

WHITLOCKITE CERAMIC

BACKGROUND OF THE INVENTION

1. Field of the Invention

The subject matter of this invention resides in the field of inorganic chemistry, especially ceramics, and finds particular utility in the area of orthopedics.

2. Description of the Prior Art

Much current research in the field of biomaterials is focused on the preparation of biocompatible ceramics which can be used as a substitute for bone.

The calcium phosphates, e.g., whitlockite [tricalcium phosphate $Ca_3(PO_4)_2$], which closely resemble biological hard tissue in chemical composition are of particular interest and have been the subject of numerous investigations. Previous attempts to produce whitlockite in macroform have generally involved powder preparation and compaction and sintering under pressure. The products produced have usually been porous and lacking the strength characteristics required of many orthopedic implant devices.

Thus, T. D. Driskell, et al., Proceedings of the 26th Annual Conference on Engineering in Medicine and Biology 15, 199 (1973) and C. R. Hassler et al., Proceedings of the 27th Annual Conference on Engineering in Medicine and Biology 16, 488 (1974), disclose a porous, resorbable tricalcium phosphate ceramic implant material prepared by sintering isostatically compacted blocks consisting of laboratory-prepared calcium phosphate powder and naphthalene as the pore-forming agent. The resulting material is stated to have 36% large porosity, 14% fine matrix porosity and a compressive strength of 3000 psi.

Use of the above ceramic as an implant material in bone is described in the following three references: S. N. Bhaskar et al., Oral Surgery 32, 336–346 (1971); L. Getter et al., J. Oral Surgery 30, 263–268 (1972); and M. P. Levin et al., J. Biomed. Mater. Res. 9, 183–195 (1975).

W. Mors et al., J. Dent. Res. 53, 129 (1974) (Special Issue) Abstract 297 and J.A.M.A. 236, 2373 (1976), disclose the use of a porous resorbable tricalcium phosphate ceramic to repair surgically created cleft palates in dogs.

Driskell, et al., U.S. Pat. No. 3,913,229 issued Oct. 21, 1975, disclose a dental composition in the form of a colloidal paste containing a powdered calcium phosphate, e.g. tricalcium phosphate prepared by calcination of particles of the compound to give a unitary body which is ground into a powder.

D. M. Roy et al., Nature 247, 220–222 (1974) and U.S. Pat. No. 3,929,971 issued Dec. 30, 1975, describe an elaborate hydrothermal exchange process whereby the skeletal calcium carbonate of certain marine coral is converted to whitlockite. The material so-produced necessarily retains the high porosity characteristics of the coral structure.

Jarcho, Belgian Pat. No. 831,944 published Feb. 2, 1976, discloses a strong, dense, non-porous polycrystalline sintered ceramic comprising a mixture of whitlockite and hydroxylapatite useful as a dental and surgical implant material and which is prepared by precipitating the calcium phosphate from aqueous solution and sintering the resulting product at 1000° C.–1350° C.

J. C. Heughebaert et al., Bull. Soc. Chim. France, 2923–2924 (1970), disclose a process for preparing whitlockite which comprises rapidly mixing stoichiometric amounts of calcium and phosphate ions and separating the resulting precipitate as it is formed.

J. A. Lechuga Panos, Spanish Pat. No. 381,030 published June 16, 1972, discloses the preparation of high purity tricalcium phosphate which comprises reacting calcium oxide with phosphoric acid at pH 7–7.5.

P. Leclerq, Thermal Analysis 2, 229–238 (1971), describes the various transformations which take place upon heating a mixture of tricalcium phosphate and ammonium sulfate in a molar ratio of 1 to 4.5 in the temperature range 230° C. to 1100° C. to ultimately regenerate tricalcium phosphate. The physical nature of the latter is not disclosed.

SUMMARY OF INVENTION

In an article of manufacture aspect, the invention sought to be patented resides in a translucent, isotropic, substantially pore-free, polycrystalline ceramic comprising whitlockite containing within the crystal lattice thereof about 0.1 to 2.2 percent by weight sulfate ion and characterized by an average crystallite size in the approximate range 0.3 to 3 microns and a density greater than about 98 percent of the theoretical density of β-whitlockite. This ceramic is useful as a strong resorbable dental and surgical prosthetic material.

In another article of manufacture aspect, the invention sought to be patented resides in a polycrystalline foamed ceramic body comprising whitlockite containing within the crystal lattice thereof about 0.1 to 2.2 percent by weight sulfate ion and characterized by an average crystallite size in the approximate range 0.3 to 3 microns, a total pore volume in the approximate range 20 to 80 percent, said pore volume comprising a substantially uniform distribution of open pores having a pore size diameter in the approximate range 50 to 300 microns. This ceramic is useful as a resorbable dental and surgical prosthetic material.

In a process aspect, the invention sought to be patented resides in a process for producing a translucent, isotropic, substantially pore-free, polycrystalline ceramic comprising whitlockite containing within the crystal lattice thereof about 0.1 to 2.2 percent by weight sulfate ion and characterized by an average crystallite size in the approximate range 0.3 to 3 microns and a density greater than about 98 percent of the theoretical density of β-whitlockite which comprises reacting calcium ion with phosphate ion in a molar ratio in the approximate range 1.2–1.5 to 1 in aqueous medium at a pH of about 10 to 12 to produce a gelatinous precipitate of calcium phosphate having a molar ratio of calcium to phosphorus in the approximate range 1.50–1.53 to 1, separating the gelatinous precipitate from the solution, washing the precipitate free of soluble salts with water, homogeneously suspending the washed precipitate in 1 to 3 percent (w/w) aqueous ammonium sulfate in the amount of about 10 to 20 ml. per gram of theoretically expected whitlockite ceramic, separating the precipitate from the ammonium sulfate solution, drying the precipitate and heating the dried precipitate at a temperature in the approximate range 1000° C. to 1350° C. for about 0.5 to 4 hours.

In a further process aspect, the invention sought to be patented resides in a process for producing a polycrystalline foamed ceramic body comprising whitlockite containing within the crystal lattice thereof about 0.1 to 2.2 percent by weight sulfate ion and characterized by an average crystallite size in the approximate range 0.3 to 3 microns, a total pore volume in the approximate range 20 to 80 percent, said pore volume comprising a substantially uniform distribution of open pores having a pore size diameter in the approximate range 50 to 300 microns which comprises reacting calcium ion with phosphate ion in a molar ratio of about 1.2–1.5 to 1 in aqueous medium at a pH of about 10–12 to produce a gelatinous precipitate of calcium phosphate having a calcium to phosphorus molar ratio of about 1.50–1.53 to 1, separating the gelatinous precipitate from the solution, washing the precipitate free of soluble salts with water, homogeneously suspending the washed precipitate in 1 to 3 percent (w/w) aqueous ammonium sulfate in the amount of about 10 to 20 ml. per gram of theoretically expected whitlockite ceramic, separating the precipitate from the ammonium sulfate solution, mixing the precipitate with about 0.5 to 10 percent by weight of a blowing agent and about 0.5 to 10 percent by weight of a foam stabilizer, heating the resulting mixture at about 70° C. to 90° C. until decomposition of the blowing agent and drying of the resultant foam are substantially complete, and then heating the dried foam at about 1000° C. to 1350° C. until volatilization of the foam stabilizer and sintering of the resulting product are substantially complete.

In yet a further process aspect, the invention sought to be patented resides in a process for producing non-ceramic crystalline whitlockite containing within the crystal lattice thereof about 0.1 to 2.2 percent by weight sulfate ion which comprises reacting calcium ion with phosphate ion in a molar ratio in the approximate range 1.2–1.5 to 1 in aqueous medium at a pH of about 10 to 12 to produce a gelatinous precipitate of calcium phosphate having a molar ratio of calcium to phosphorus in the approximate range 1.50–1.53 to 1, separating the gelatinous precipitate from the solution, washing the precipitate free of soluble salts with water, homogeneously suspending the washed precipitate in 1 to 3 percent (w/w) aqueous ammonium sulfate in the amount of about 10 to 20 ml. per gram of theoretically expected whitlockite ceramic, separating the precipitate from the ammonium sulfate solution, drying the precipitate and heating the dried precipitate at a temperature in the approximate range 725° C. to 900° C. for about 0.5 to 4 hours.

In one of its method aspects, the invention sought to be patented provides an improvement in the method for filling a void in a living bone which method includes the step of filling the void with a biocompatible ceramic, the improvement residing in the use of either a biocompatible, substantially pore-free, polycrystalline ceramic comprising whitlockite containing within the crystal lattice thereof about 0.1 to 2.2 percent by weight sulfate ion and characterized by an average crystallite size in the approximate range 0.3 to 3 microns and a density greater than about 98 percent of the theoretical density of β-whitlockite or a biocompatible polycrystalline foamed ceramic body comprising whitlockite containing within the crystal lattice thereof about 0.1 to 2.2 percent by weight sulfate ion and characterized by an average crystallite size in the approximate range 0.3 to 3 microns, a total pore volume in the approximate range 20 to 80 percent, said pore volume comprising a substantially uniform distribution of open pores having a pore size diameter in the approximate range 50 to 300 microns.

In a further method aspect, the invention sought to be patented provides an improvement in the method for prosthetically reconstructing a defective living bone which method includes the step of implanting an artificial bone prosthesis, the improvement residing in implanting a resorbable artificial bone prosthesis in the form of either a biocompatible substantially pore-free, polycrystalline ceramic comprising whitlockite containing within the crystal lattice thereof about 0.1 to 2.2 percent by weight sulfate ion and characterized by an average crystallite size in the approximate range 0.3 to 3 microns and a density greater than about 98 percent of the theoretical density of β-whitlockite or a biocompatible polycrystalline foamed ceramic body comprising whitlockite containing within the crystal lattice thereof about 0.1 to 2.2 percent by weight sulfate ion and characterized by an average crystallite size in the approximate range 0.3 to 3 microns, a total pore volume in the approximate range 20 to 80 percent, said pore volume comprising a substantially uniform distribution of open pores having a pore size diameter in the approximate range 50 to 300 microns.

DETAILED DESCRIPTION OF THE INVENTION INCLUSIVE OF THE PREFERRED EMBODIMENTS

Whitlockite exists in two crystalline modifications, the alpha form, a metastable state occurring at high temperatures, and the beta form, the thermodynamically stable state. Unless otherwise indicated the term "whitlockite" as used herein is intended to comprehend either the alpha or the beta form or any mixture of these.

The novel, translucent, isotropic, substantially pore-free, polycrystalline ceramic of this invention comprises whitlockite containing within the crystal lattice thereof about 0.1 to 2.2 percent by weight sulfate ion and characterized by an average crystallite size in the approximate range 0.3 to 3 microns and a density greater than about 98 percent of the theoretical density of β-whitlockite. This whitlockite ceramic is further characterized by a compression strength in the approximate range 90,000 to 130,000 psi and a tensile strength in the approximate range 10,000 to 30,000 psi.

In view of the known dependence of compression and tensile strengths on the shape, dimensions and surface characteristics of the material tested it will be appreciated that the substantially fully dense ceramic whitlockite provided by this invention, when suitably fabricated, has compression and tensile strengths substantially greater than 130,000 and 30,000 psi respectively.

The ceramic whitlockite of the present invention can be fabricated in any desired form or shape employing conventional modes of fabrication such as molding, casting, machining, milling and the like. In such manner the ceramic can be produced as, for example, a flat sheet of any desired thickness, a cylinder, a cone, a sphere, granules, powder, etc.

In addition to having the above-described properties, the whitlockite ceramic of this invention is also completely biocompatible and resorbable, and therefore eminently suitable as a surgical implant material, especially for bone reconstruction and repair. Thus a defect or void in a bone is filled with the ceramic either as a shaped body or in particulate form. As the ceramic is slowly resorbed, it is replaced by new biological hard tissue.

The high strength characteristics of the above-described ceramic, which are due to its unique microstructure, i.e. to its small crystallite size and substantially complete non-porosity, are of prime importance in prosthetic materials which are implanted at sites subject to stress such as load-bearing bones. However, in certain applications, circulation of body fluids, tissue ingrowth and stimulation of new bone formation, such as would be optimally promoted by a porous implant material, are paramount. For such use, as described in detail hereinbelow, a ceramic whitlockite can be afforded by this invention essentially as a ceramic foam having a total pore volume of about 20 to 80 percent, said pore volume comprising a substantially uniform distribution of open pores (pores connected to an exterior surface) with an average pore size diameter of about 50 to 300 microns. This material is of particular utility in the repair of periodontal lesions or reconstruction of facial bone and constitutes a further composition aspect of the present invention. It will, of course, be appreciated that the introduction of pores into the ceramic whitlockite will effect a reduction in compression and tensile strengths. Nevertheless, due to the small crystallite size and the absence of appreciable fine matrix porosity, the porous ceramic retains substantial mechanical strength.

As described in detail hereinbelow, the preparation of the novel whitlockite ceramic of this invention requires the initial precipitation of the appropriate calcium phosphate from aqueous medium. The interaction of calcium ion with phosphate ion in aqueous medium is a complex and incompletely understood process usually involving a number of equilibrium reactions proceeding at varying rates and producing different products [Eanes et al., Nature 208, 365 (1965) and Bett et al. J. Amer. Chem. Soc. 89, 5535 (1967)]. As might be expected, the results of such interactions are profoundly affected by stoichiometry, i.e. the molar ratio of calcium to phosphorus (Ca/P), reaction time, temperature and pH. It is generally believed that calcium and phosphate ions initially combine to form an insoluble calcium-deficient apatite having a calcium-to-phosphorus ratio of about 1.5, the correct stoichiometry for whitlockite. However, the apatite crystal lattice appears to be the most stable configuration in the calcium phosphate system and, in the presence of sufficient excess calcium ion, the initial precipitate undergoes slow transformation to hydroxylapatite with a calcium-to-phosphorus ratio of 1.67 (Eanes et al., supra). An intermediate calcium-to-phosphorus ratio, i.e. between 1.5 and 1.67 affords a mixture of whitlockite and hydroxylapatite when the precipitate is heated (Jarcho, Belgian Pat. No. 831,944). It thus becomes apparent that in order to obtain whitlockite, a calcium-to-phosphorus ratio of 1.5 must be maintained. The apparently simple expedient of reacting calcium and phosphate ion in a molar ratio of 1.5 to 1 was found ineffective in producing pure whitlockite and instead afforded a mixture of whitlockite and hydroxylapatite. In fact, even reducing the calcium ion to phosphate ion ratio to 1.2 to 1 ultimately produced a mixture of whitlockite and hydroxylapatite. Reacting calcium ion with phosphate ion in the whitlockite stoichiometry, i.e. Ca/P=1.5, and immediately isolating the initially formed precipitate [J. C. Heughebaert and G. Montel, Bull. Soc. Chim. France, 2923-2924 (1970)], thereby presumably preventing further equilibration, was partially successful in producing pure whitlockite. However, this procedure was found not readily reproducible and is unsuited to large scale commercial production.

It has now been discovered that the addition of a small amount of sulfate ion to the calcium phosphate precipitate followed by collecting and heating, results in complete conversion of the latter to whitlockite containing no detectable trace of hydroxylapatite. Moreover, the sintering of the whitlockite so-produced affords a high-quality ceramic having superior physical and mechanical properties and which is eminently suitable as a biological implant material.

Thus, the process of this invention for preparing substantially pure whitlockite (containing within its crystal lattice about 0.1 to 2.2 percent by weight sulfate ion) as a strong, translucent, isotropic, substantially pore-free, polycrystalline ceramic comprises reacting calcium ion with phosphate ion in a molar ratio of about 1.2-1.5 to 1 in aqueous medium at a pH of about 10-12 to produce a gelatinous precipitate of calcium phosphate having a molar ratio of calcium to phosphorus in the approximate range 1.50-1.53 to 1, separating said gelatinous precipitate from the solution, washing said precipitate free of soluble salts with water, homogeneously suspending the washed precipitate in approximately 1 to 3 percent aqueous ammonium sulfate in the amount of about 10 to 20 ml. per gram of expected whitlockite, separating the precipitate from the ammonium sulfate solution, drying said precipitate and heating the dried precipitate in the approximate range 1000° C. to 1350° C. for about 0.5 to 4 hours.

Thus, whitlockite is precipitated from aqueous medium by reacting calcium ion with phosphate ion at a pH of about 10-12. Any calcium—or phosphate—containing compounds which provide calcium and phosphate ions in aqueous medium are suitable provided that the respective counter ions of said compounds are easily separated from the whitlockite product, are not themselves incorporated in the whitlockite lattice, or do not otherwise interfere with the precipitation or isolation of the whitlockite. Compounds which provide calcium ion are, for example, calcium nitrate, calcium hydroxide, calcium acetate and the like. Phosphate ion can be provided by diammonium hydrogen phosphate, ammonium phosphate, phosphoric acid and the like. In the present method, calcium nitrate and diammonium hydrogen phosphate are the preferred sources of calcium and phosphate ions respectively.

First, calcium nitrate and diammonium hydrogen phosphate in a molar ratio of about 1.2-1.5 to 1 are interacted in aqueous solution at a pH of about 10-12 to produce a gelatinous precipitate of calcium phosphate. Temperature is not critical and the precipitation can be carried out from about 0° C. to 100° C., but is preferably carried out at about room temperature. The gelatinous precipitate thus obtained is separated from the solution by suitable means, for example by centrifugation and decantation of the supernatant. The residual mineral sludge can be washed free of any remaining soluble salts by suspending in distilled water, centrifuging and decanting the supernatant. Although not essential to the process, the latter step appears to minimize cracking during subsequent sintering. The residual product can then be suspended in a minimum amount of distilled water and stored for future use. Conversion to crystalline whitlockite is effected by first homogeneously suspending the mineral sludge in 1 to 3 percent (w/w) aqueous ammonium sulfate. Ordinarily, 10 to 20 ml. of 1 to 3 percent (w/w) aqueous ammonium sulfate per gram of theoretically expected whitlockite ceramic is employed. The solid is then separated from the solution by centrifugation and vacuum filtration. The gelatinous product thus collected contains a large amount of occluded water, much of which can be removed by pressing. The resulting wet clay-like material is cut or shaped into a convenient form or, alternatively cast in a suitable mold. A shrinkage of approximately 25 percent occurs when the wet product is dried and a further shrinkage of about 25 percent takes place during the sintering hereinafter described, and this should of course, be taken into account when shaping or molding the material. The wet product is slowly heated up to the sintering temperature of 1000° C. to 1350° C. at which point all remaining water will have been driven off. Maintaining the temperature at 1000° C. to 1350° C. for approximately 0.5 to 4 hours will then effect the sintering and substantially maximum densification of the product. Ordinarily, it is convenient to isolate the dried product prior to sintering. Thus, the wet product is dried at about 90° C. to 900° C. for approximately 3 to 24 hours or until the water content thereof has been reduced to about 6 percent. It is generally preferred to use drying conditions of approximately 90° C. to 95° C. for about 15 hours or until the water content has been reduced to about 6 percent. The whitlockite obtained in this manner is brittle and porous, but has considerable mechanical strength. Some separation or cracking of the clay-like material may occur on drying especially if a thick filter cake is used. Separation or cracking during drying can be minimized or prevented by adding to the suspension of freshly precipitated calcium phosphate small amounts of conventional binders known in the ceramics art such as polyethylene glycol or polyvinyl alcohol.

It is usually convenient at this stage to further cut or shape the dried whitlockite into roughly the form desired as the end product, taking into account the shrinkage mentioned above which occurs on sintering.

The bodies of whitlockite prior to sintering should be uniform and free of defects. The presence of cracks or fissures can cause the pieces to fracture during the sintering process. The products are then sintered at about 1000° C. to 1350° C. for approximately 0.5 to 4 hours. Sintering is preferably effected at 1150° C. to 1200° C. for approximately 1 hour. There are thus produced articles of the hard, dense ceramic as described hereinabove. These articles can then be polished or machined using conventional techniques.

The ceramic initially produced upon heating at about 1000° C. comprises a mixture of the metastable α-whitlockite and the thermodynamically stable β-whitlockite. If desired, the ceramic can be equilibrated by heating below the sintering temperature, for example, at about 900° C. for approximately 4 hours to afford substantially pure β-whitlockite ceramic.

It is important in the chemical process described above that the calcium to phosphorus ratio of the isolated precipitate correspond as closely as possible to the theoretical value for whitlockite, i.e. Ca/P=1.50, in order to minimize the hydroxylapatite content of said precipitate and thereby minimize the amount of ammonium sulfate required to produce the substantially pure whitlockite of this invention. Thus, if the calcium to phosphorus ratio of the precipitate is substantially greater than about 1.53, exposure to 1 to 3 percent aqueous ammonium sulfate is inadequate to produce pure whitlockite and affords instead a mixture of whitlockite and hydroxylapatite. A calcium phosphate precipitate having a calcium to phosphorus ratio greater than 1.53 can be converted completely to whitlockite by employing a larger amount of ammonium sulfate. In fact, a precipitate of pure hydroxylapatite (Ca/P=1.67) can be converted to whitlockite by using sufficiently large quantities of ammonium sulfate. However, the whitlockite produced thereby is contaminated with significant amounts of calcium sulfate and lacks the superior physical and mechanical properties of the whitlockite ceramic afforded by the present invention. Accordingly, in order to ensure that the calcium to phosphorus ratio does not exceed about 1.53, the calcium and phosphate salts are mixed in a molar ratio of 1.5 to 1 or less, preferably 1.2–1.4 to 1. The calcium phosphate precipitiate so-produced has a calcium to phosphorus ratio of about 1.50 to 1.53, and following treatment with 1 to 3 percent aqueous ammonium sulfate (about 10–20 ml. per gram of theoretically expected whitlockite) ultimately affords the substantially pure whitlockite of this invention.

It is critical, in the chemical process described above to prepare the whitlockite as a gelatinous precipitate from aqueous solution for it is only in this cohesive gelatinous state that whitlockite can be shaped or molded and then dried and sintered to produce a ceramic body. Dry, particulalate or granular whitlockite cannot be reconstituted into this cohesive gelatinous state. If, for example, powdered whitlockite is suspended in water and filtered there is obtained a non-cohesive, particulate filter cake which simply dries and crumbles and cannot be shaped, molded or converted into a ceramic body. Moreover, although powdered whitlockite can be mechanically compressed into a shaped body, such as a tablet, when sintered, the product obtained is highly porous, opaque and does not possess the high-strength characteristics of the instantly claimed ceramic.

The process of this invention for preparing the foamed ceramic body described hereinabove comprises reacting calcium ion with phosphate ion in a molar ratio of about 1.2–1.5 to 1 in aqueous medium at a pH of about 10–12 to produce a gelatinous precipitate of calcium phosphate having a calcium to phosphorus molar ratio of about 1.50–1.53 to 1, separating the gelatinous precipitate from the solution, washing the precipitate free of soluble salts with water, homogeneously suspending the washed precipitate in approximately 1 to 3 percent (w/w) aqueous ammonium sulfate in the amount of about 10 to 20 ml. per gram of theoretically expected whitlockite ceramic, separating the precipitate from the ammonium sulfate solution, mixing the precipitate with about 0.5 to 10 percent by weight of a blowing agent and about 0.5 to 10 percent by weight of a foam stabilizer, heating the resulting mixture at about 70° C. to 90° C. until decomposition of the blowing agent and drying of the resultant foam are substantially complete, and then heating the dried foam at about 1000° C. to 1350° C. until volatilization of the foam stabilizer and sintering of the resulting product are substantially complete.

The calcium phosphate precipitate can be mixed with any conventional and readily available foam stabilizer, e.g. albumen, polyvinyl alcohol or polyethylene glycol, and any conventional blowing agents such as azodicarbonamide, hydrogen peroxide or ammonium carbonate. Upon heating the mixture, the blowing agent releases gaseous decomposition products which are trapped by the foam stabilizer thereby creating a stable foam. The latter is dried and ultimately sintered to produce a porous ceramic.

Alternatively, the blowing agent can be omitted and the foam created mechanically by whipping air into the mixture. It is also possible to omit the foam stabilizer and to employ as pore-forming agents fibrous organic materials such as starch, collagen and cellulose or volatile organic compounds such as naphthalene.

Thus, the ceramic of this invention can be conveniently obtained in a porous form as follows:

Calcium phosphate is precipitated, washed free of soluble salts and washed with aqueous ammonium sulfate as described above. The resulting mineral sludge is mixed with about 10 to 100 mg., preferably about 15 to 20 mg., of spray-dried egg white per gram of theoretically expected whitlockite ceramic and at least an equal amount, i.e. about 10 to 200 mg., preferably 15 to 30 mg., of azodicarbonamide. Additional water can be added if desired to adjust the consistency of the mixture to permit efficient stirring and transfer of the latter without introduction of large air bubbles therein. The spray-dried egg white is difficult to wet and therefore somewhat difficult to homogeneously mix with the whitlockite sludge. Accordingly, it is advantageous, though not necessary, to reconstitute the dried egg white prior to its addition to the whitlockite sludge. This is conveniently achieved by thoroughly mixing with about 10 times its weight of water. The resulting reconstituted egg white can then be easily and homogeneously mixed with the whitlockite sludge. The resulting mixture is then dried by heating at about 70° C. to 90° C. for approximately 8 to 20 hours. If desired, the mixture can be poured into a suitable mold prior to drying. Ordinarily, the mixture is covered loosely in order to prevent drying out before decomposition of the azodicarbonamide is complete. Alternatively, drying can be carried out in a high-humidity chamber. The dried product is finally sintered by heating at a temperature in the approximate range 1000° C. to 1350° C. for about 0.5 to 2 hours, preferably at 1050° C. to 1150° C. for 1 hour. At this point any residual foaming agent or foam stabilizer will have been volatilized and the whitlockite will have undergone substantially complete sintering. The resulting porous ceramic body can be further cut or machined into any desired shape.

As noted above for the fully dense material, the porous material can be produced either as pure $\beta$-whitlockite or as a mixture of the latter and $\alpha$-whitlockite.

As noted hereinabove, the ceramic afforded by the present invention, in either the pore-free or porous form, is useful as a resorbable biological implant material. The rate of resorption is partially dependent on the crystalline phase of the whitlockite ceramic, the $\alpha$ form resorbing more rapidly than the $\beta$ form. Accordingly, it is possible to control the rate or resorption of a whitlockite ceramic implant device by varying the ratio of $\alpha$-to-$\beta$-whitlockite therein.

The process of this invention for preparing non-ceramic crystalline whitlockite containing within the crystal lattice thereof about 0.1 to 2.2 percent by weight sulfate ion comprises the above-described steps for producing the dried calcium phosphate precipitate and then heating the latter to at least about 725° C., the temperature at which the initially obtained precipitate undergoes a phase transformation to crystalline whitlockite as indicated by differential thermal analysis and X-ray diffraction, but below about 1000° C., the temperature at which whitlockite begins to sinter. This process affords a simplified, reliable and economical method of producing substantially pure (i.e. 97.2–99.9 percent pure) whitlockite.

The invention is further illustrated by the following examples without, however, being limited thereto.

EXAMPLE 1

An aqueous solution containing 0.24 mole of diammonium hydrogen phosphate (235 ml. of a 1.02 M solution) was brought to pH 11 with 150 ml. of concentrated aqueous ammonia. An additional 600 ml. of water was added to dissolve precipitated ammonium phosphate. The resulting solution was added dropwise over 0.5 hour to a stirred solution containing 356 ml. of 1.01 M aqueous calcium nitrate (0.36 mole)(Ca/P=1.5) diluted with 350 ml. of water and previously adjusted to pH 11 with 15 ml. of concentrated aqueous ammonia. Stirring was continued for a short time after the addition was complete and then the resulting suspension was allowed to stand overnight at room temperature. The mixture was rapidly stirred for about 20 min. to regenerate a homogeneous suspension. One quarter of the suspension was removed, centrifuged and the supernatant decanted. The residue was suspended in 200 ml. of 5 percent (w/w) aqueous ammonium sulfate. The suspension was centrifuged and the supernatant decanted. The residue was filtered and dried at room temperature overnight. The resulting dried material was heated 1 hr. at 900° C. to give a product shown by conventional X-ray diffraction analysis to be 100 percent $\beta$-whitlockite (As given here and hereinafter, percentage composition determined by X-ray diffraction is, of course, within the limits of accuracy of the diffractometer, i.e. $\pm 2$ percent). The product had a calcium to phosphorus ratio (Ca/P) of $1.53 \pm 0.03$ as shown by standard elemental analysis.

EXAMPLE 2

Four 250-ml. aliquots were withdrawn from a well stirred, homogeneous suspension prepared by reacting 264.1 g. (2 moles) of diammonium hydrogen phosphate with 3.4 l. of 0.88 M aqueous calcium nitrate (3 moles)-(Ca/P=1.5) essentially as described in Example 1. The four aliquots were treated respectively with 100 g. of 0.5, 1, 2 and 3 (w/w) aqueous ammonium sulfate. The aliquots were then shaken to insure homogeneity, the solids collected by filtration, pressed dry under vacuum and then dried overnight at 90° C. A sample of each of the solids so-produced was sintered at 1100° C. for one hour. The products resulting from the aliquots treated with 1, 2 and 3 percent aqueous ammonium sulfate respectively were shown by conventional X-ray diffraction analysis to be 100 percent $\beta$-whitlockite. The material which had been treated with 0.5 percent aqueous ammonium sulfate contained approximately 89 percent $\beta$-whitlockite and 11 percent hydroxylapatite. Standard elemental analysis of the material resulting from treatment with 1 percent aqueous ammonium sulfate indicated Ca/P=$1.54 \pm 0.03$ and a sulfate content of 0.67 percent by weight.

A 5-liter aliquot of the above suspension was centrifuged and the supernatant decanted. The residue was suspended with thorough agitation in 1250 ml. of 1 percent (w/w) aqueous ammonium sulfate. The suspension was degassed by stirring gently under reduced pressure for 2 hours, and the solids were collected by filtration and dried at 85° C. to give 96 g. of product which was then heated, at 800° C. for 2 hours and at 1100° C. for 1 hour. Sintering was completed by heating 1 hour at 1150° C. followed by equilibration at 900° C. for 4 hours.

A sample was fractured and the fracture surface was thermally etched by heating at 1100° C. for 1.5 hours. The etched sample was then mounted with silver paste on a scanning electron microscope sample holder, coated with a thin layer of gold and observed in an AMR 1000 scanning electron microscope. The sample had an average grain size of 0.424 micron and contained no pores. A sample which had been sintered at 1200° C. for 1 hour and then equilibrated at 900° C. for 4 hours had an average grain size of 0.483 micron and was also pore-free.

The densities of the samples sintered at 1150° C. and 1200° C. as determined by the standard liquid displacement method, were 3.04 g./cm$^3$ and 3.06 g./cm$^3$ respectively.

EXAMPLE 3

A 1-liter aliquot of a well-stirred, homogeneous suspension prepared by reacting 264.1 g. (2 moles) of diammonium hydrogen phosphate with 3.4 l. of 0.88 M aqueous calcium nitrate (3 moles)(Ca/P=1.5) essentially as described in Example 1 was centrifuged at 2000 rpm for 10 min. and the supernatant decanted. The residue was treated with 250 ml. of 1 percent (w/w) aqueous ammonium sulfate, shaken thoroughly, degassed for 1 hr., filtered and dried overnight at 95° C. to give 19.6 g. of white solid. Sintering at 1100° C. for 1 hr. afforded a strong, white, translucent ceramic product. Standard elemental analysis of the latter indicated Ca/P=1.55 (±0.03) and conventional X-ray diffraction analysis showed the product to be 100 percent $\beta$-whitlockite. Five polished cylindrical plugs 4.6 mm. in diameter and 1.64 mm. in height were prepared and tested for compression strength employing conventional techniques. The average compression strength was found to be 95,900±4900 psi.

Another sample prepared essentially as the above-described was shown by X-ray diffraction to be 100 percent $\beta$-whitlockite and had Ca/P=1.52 (±0.03) and an average compression strength of 99,600±13,200 psi.

EXAMPLE 4

An aqueous solution containing 0.5 mole of diammonium hydrogen phosphate (174 ml. of a 2.88 M solution) was diluted to 750 ml. with distilled water, brought to pH 11 with 600 ml. of concentrated aqueous ammonia and further diluted to 2500 ml. with water to give a clear solution. The latter was added in a fine stream over 15 min. to a stirred solution containing 403 ml. of 1.735 M aqueous calcium nitrate (0.7 mole)(Ca/P=1.4) diluted to 1250 ml. with distilled water and previously adjusted to pH 11 with 20 ml. of concentrated aqueous ammonia. The resulting suspension was stirred overnight at room temperature. A 100 ml. aliquot of the homogeneous suspension was withdrawn and centrifuged. The supernatant was decanted and the residue was suspended with thorough agitation in 25 ml. of 1 percent (w/w) aqueous ammonium sulfate. The product was collected by filtration and dried overnight at 60° C. The resulting white solid was sintered 1 hr. at 1150° C. affording a ceramic product shown by conventional X-ray diffraction analysis to be 100 percent whitlockite, approximately 96 percent of which was in the $\beta$ form and 4 percent in the $\alpha$ form. Standard elemental analysis showed Ca/P=1.48 (±0.03).

Another aliquot of the suspension was worked up as above described and the resulting product was sintered by heating slowly to 1125° C., maintaining that temperature for 1 hour and then cooling and maintaining the sample at 900° C. for 4 hours. The resulting ceramic had Ca/P=1.51 and a sulfate content of 1.2 percent by weight. X-ray diffraction indicated the product to be 100 percent $\beta$-whitlockite. Crackfree samples of this material were polished to 600 grit SiC and subjected to the standard 3 point bend test. The samples displayed an average tensile strength of 19,800 ±5700 psi. The density of this material as determined by the standard liquid displacement method was found to be 3.050±0.002 g/cm$^3$.

EXAMPLE 5

An aqueous solution containing 0.5 mole of diammonium hydrogen phosphate (174 ml. of a 2.88 M solution) was diluted to 750 ml. with distilled water, adjusted to pH 11 with 600 ml. of concentrated ammonia and further diluted to 2500 ml. with distilled water to give a clear solution. This solution was added over 0.5 hr. to a stirred aqueous solution containing 0.6 mole of calcium nitrate (346 ml. of a 1.735 M solution)(Ca/P=1.2) diluted to 1250 ml. with distilled water and previously adjusted to pH 11 with 20 ml. of concentrated ammonia and the resulting mixture stirred overnight. After standing several days the mixture was stirred 1 hr. to give a homogeneous suspension. A 500 ml. aliquot was withdrawn, centrifuged, the supernatant decanted and the residue suspended with thorough agitation in 125 ml. of 2 percent (w/w) aqueous ammonium sulfate. The product was collected by filtration, dried at 50° C. overnight and then sintered at 1150° C. for 1 hr. followed by equilibration at 900° C. for 4 hours to give 7.2 g. of white, translucent ceramic consisting of 100 percent $\beta$-whitlockite as shown by X-ray diffraction and having Ca/P=1.50 and a sulfate content of 0.10 percent by weight as indicated by elemental analysis.

EXAMPLE 6

A solution containing 264.1 g. (2 moles) of diammonium hydrogen phosphate in sufficient distilled water to give a total volume of 5.4 l. was brought to pH 11 with 3.0 l. of concentrated aqueous ammonia. The resulting precipitate was dissolved by diluting with distilled water to a volume of 10.1. The resulting solution was added in a fine stream to a stirred solution containing 1499 ml. of 1.735 M aqueous calcium nitrate diluted to 5.4 l. with distilled water and previously adjusted to pH 11 with 90 ml. of concentrated ammonia. After the addition was complete, the reaction mixture was stirred an additional 5 hours and then allowed to stand overnight at room temperature. The supernatant was decanted and the remaining suspension was centrifuged. The supernatant was decanted and the residual sludge was washed twice by suspending in distilled water, centrifuging and decanting the supernatant. The washed sludge was then suspended in 1500 ml. of distilled water. The suspension was rapidly stirred to insure homogeneity and a 175 ml. aliquot was drawn off. The aliquot was centrifuged, the supernatant decanted and the residue suspended in 100 ml. of 1 percent (w/w) aqueous ammonium sulfate. The resulting suspension was centrifuged and the supernatant was decanted. The residual sludge was mixed with 180 mg. of spray-dried egg white (previously reconstituted by thoroughly mixing with 10 ml. of distilled water) followed by 180 mg.

of azodicarbonamide. The resulting mixture was stirred vigorously for about 0.25 hr. and then poured into cube-shaped molds, loosely covered and dried at 80° C. overnight. The resulting dried foam was sintered at 1050° C. for 1 hr. to give a porous whitlockite ceramic having an average pore size of about 100 microns.

EXAMPLE 7

Following a procedure similar to that described in Example 6 and sintering samples of the resulting dried whitlockite foam for 1 hr. at 1050° C., 1100° C. and 1125° C. afforded three porous whitlockite ceramic bodies having bulk densities of 1.41, 1.6 and 1.72 g/cm$^3$ respectively, and apparent porosities of 54.7, 52.0 and 35.1 percent respectively, as determined by standard ASTM methods.

The biocompatibility of the whitlockite ceramic afforded by the present invention was confirmed by implanting in voids in the femurs of live dogs, plugs and granules of porous whitlockite ceramic prepared in accordance with the above-described procedures. The implant sites were characterized by normal healing and the absence of any evidence of inflammation or foreign body response, and resorption of the implant material was nearly complete at two months and replacement thereof by new dense bone was evident. At seven months, remodeling of the new dense bone which filled the spaces formerly occupied by the whitlockite ceramic and of the bone surrounding the original implant site was more advanced than at two months.

We claim:

1. A translucent, isotropic, substantially pore-free polycrystalline ceramic consisting essentially of whitlockite containing within the crystal lattice thereof about 0.1 to 2.2 percent by weight sulfate ion and characterized by an average crystallite size in the approximate range 0.3 to 3 microns and a density greater than about 98 percent of the theoretical density of β-whitlockite.

2. A ceramic according to claim 1 wherein the whitlockite is β-whitlockite.

3. A ceramic according to claim 1 shaped or formed substantially into a flat sheet.

4. A ceramic according to claim 1 shaped or formed substantially into a cylindrical rod.

5. A strong, dense, resorbable artificial bone prosthesis in the form of a polycrystalline ceramic according to claim 1.

6. A polycrystalline foamed ceramic body consisting essentially of whitlockite containing within the crystal lattice thereof about 0.1 to 2.2 percent by weight sulfate ion and characterized by an average crystallite size in the approximate range 0.3 to 3 microns, a total pore volume in the approximate range 20 to 80 percent, said pore volume comprising a substantially uniform distribution of open pores having a pore size diameter in the approximate range 50 to 300 microns.

7. A foamed ceramic body according to claim 6 wherein the whitlockite is β-whitlockite.

8. A foamed ceramic body according to claim 6 shaped or formed substantially into a flat sheet.

9. A foamed ceramic body according to claim 6 shaped or formed substantially into a cylindrical rod.

10. A resorbable artificial bone prosthesis in the form of a polycrystalline ceramic according to claim 6.

11. A process for producing a ceramic according to claim 1 which comprises reacting calcium ion with phosphate ion in a molar ratio in the approximate range 1.2–1.5 to 1 in aqueous medium at a pH of about 10 to 12 to produce a gelatinous precipitate of calcium phosphate having a molar ratio of calcium to phosphorus in the approximate range 1.50–1.53 to 1, separating said gelatinous precipitate from the solution, washing said precipitate free of soluble salts with water, homogeneously suspending the washed precipitate in 1 to 3 percent (w/w) aqueous ammonium sulfate in the amount of about 10 to 20 ml. per gram of theoretically expected whitlockite ceramic, separating the precipitate from the ammonium sulfate solution, drying said precipitate and heating the dried precipitate in the approximate range 1000° C. to 1350° C. for about 0.5 to 4 hours.

12. A process according to claim 11 wherein the dried precipitate is heated at about 1150° C. to 1200° C. for approximately 1 hour.

13. A process according to claim 12 wherein the product is subsequently heated at about 900° C. for approximately 4 hours whereby the resulting whitlockite ceramic consists essentially of β-whitlockite.

14. A process for producing a polycrystalline foamed ceramic body according to claim 6 which comprises reacting calcium ion with phosphate ion in a molar ratio of about 1.2–1.5 to 1 in aqueous medium at a pH of about 10–12 to produce a gelatinous precipitate of calcium phosphate having a calcium to phosphorus molar ratio of about 1.50–1.53 to 1, separating said gelatinous precipitate from the solution, washing said precipitate free of soluble salts with water, homogeneously suspending the washed precipitate in 1 to 3 percent (w/w) aqueous ammonium sulfate in the amount of about 10 to 20 ml. per gram of theoretically expected whitlockite ceramic, separating the precipitate from the ammonium sulfate solution, mixing the precipitate with about 0.5 to 10 percent by weight of a blowing agent and about 0.5 to 10 percent by weight of a foam stabilizer, heating the resulting mixture at about 70° C. to 90° C. until decomposition of the blowing agent and drying of the resultant foam are substantially complete, and then heating the dried foam at about 1000° C. to 1350° C. until volatilization of the foam stabilizer and sintering of the resulting product are substantially complete.

15. A process according to claim 14 wherein the blowing agent is azodicarbonamide and the foam stabilizer is egg albumen.

16. A process according to claim 15 wherein the mixture of the calcium phosphate precipitate, azodicarbonamide and egg albumen is dried at about 70° C. to 90° C. for approximately 8 to 20 hours and the resulting dried foam is heated at about 1050° C. to 1150° C. for approximately 1 hour.

17. A process for producing non-ceramic, crystalline whitlockite containing within the crystal lattice thereof about 0.1 to 2.2 percent by weight sulfate ion which comprises reacting calcium ion with phosphate ion in a molar ratio in the approximate range 1.2–1.5 to 1 in aqueous medium at a pH of about 10 to 12 to produce a gelatinous precipitate of calcium phosphate having a molar ratio of calcium to phosphorus in the approximate range 1.50–1.53 to 1, separating said gelatinous precipitate from the solution, washing said precipitate free of soluble salts with water, homogeneously suspending the washed precipitate in 1 to 3 percent (w/w) aqueous ammonium sulfate in the amount of about 10 to 20 ml. per gram of theoretically expected whitlockite ceramic, separating the precipitate from the ammonium sulfate solution, drying said precipitate and heating the dried precipitate in the approximate range 725° C. to 900° C. for about 0.5 to 4 hours.

18. In a method for filling a void in a living bone which includes the step of filling said void with a biocompatible ceramic, the improvement which comprises employing a biocompatible ceramic according to claim 1.

19. In a method for filling a void in a living bone which includes the step of filling said void with a biocompatible ceramic, the improvement which comprises employing a biocompatible ceramic according to claim 6.

20. In a method for prosthetically reconstructing a defective living bone which includes the step of implanting an artificial bone prosthesis, the improvement which comprises implanting an artificial bone prosthesis according to claim 5.

21. In a method for prosthetically reconstructing a defective living bone which includes the step of implanting an artificial bone prosthesis, the improvement which comprises implanting an artificial bone prosthesis according to claim 10.

* * * * *